United States Patent [19]

Krapes

[11] Plant 4,143

[45] Nov. 8, 1977

[54] CARNATION NAMED RENEGADE

[75] Inventor: David A. Krapes, Arvada, Colo.

[73] Assignee: Denver Wholesale Florists Company, Denver, Colo.

[21] Appl. No.: 730,660

[22] Filed: Oct. 7, 1976

[51] Int. Cl.[2] ..... A01H 5/00

[52] U.S. Cl. ..... Plt./73

[58] Field of Search ..... Plt./73

*Primary Examiner*—Robert E. Bagwill

*Attorney, Agent, or Firm*—Chas. W. Rummler

[57] ABSTRACT

A new variety of carnation plant distinguished by its profuse and continuous production from Spring through Fall of solid red blossoms about 3 inches in diameter borne on long stems branching from very tall and sturdy canes and by the virtually complete absence of splits and bullheads.

1 Drawing Figure

BACKGROUND OF THE NEW PLANT

This new variety of red carnation plant originated as a sport of a Crowley Sim plant grown in my greenhouse at Arvada, Colo., and was discovered by me in March, 1969. Because of its strong and distinctive color, I selected this sport for reproduction, which was done by me by means of cuttings. The resulting plant proved to retain the advantageous characteristics of its parent plant variety as well as the flower form and color of the original sport and asexual propagation of this new plant through many generations at Denver, Colo., has demonstrated that its novel and advantageous characteristics hold true from generation to generation and are firmly fixed. Propagation of this new plant by cuttings is now being done on a commercial scale at Denver, Colo.

DESCRIPTION OF THE DRAWING

My new variety of carnation plant is illustrated by the accompanying photographic drawing which shows, in full color, a partially opened bud, a half opened flower, and a fully opened bloom, the flower color being as nearly true as it is reasonably possible to be had by conventional professional photographic procedures.

DESCRIPTION OF THE NEW PLANT

The following is a detailed description of my new carnation plant variety based upon observations of greenhouse plants grown under conventional greenhouse practices at Denver, Colo., these observations having been made during the Summer of 1976. The color designations stated are according to the R.H.S. Colour Chart published by The Royal Horticultural Society of London, England.

THE PLANT

Origin: Sport.

Parentage: A Crowley Sim (unpatented) of a light pink (RHS 36D) color grown in greenhouse for cut flower production.

Classification:

*Botanic.*—*Dianthus caryophyllus.*

*Commercial.*—Greenhouse carnation.

Form: Upright bush.

Height: About 140 cm., with flowering canes about 110 cm. long and about 7½ mm. in diameter.

Growth: Vigorous, sturdy and erect.

*Growth rate.*—14 weeks to flower.

Branching: Normal, the main stem having 4 to 5 shoots or branches from the lower portion of its length.

Foliage: Abundant in quantity with more than 100 leaves.

*Leaf size.*—Medium.

*Leaf shape.*—Lanceolate with acuminate apex and smooth margins.

*Texture.*—Smooth.

*Rib.*—One prominent central mid-rib.

*Color.*—Upper side — Blueish-Green; under side — Light Green.

*Petioles.*—None. The leaves are amplexicaul extending upwardly along the stem and then curving outwardly and downwardly.

*Leaflets.*—None.

THE BUD

Size: Large, about 26 mm. in diameter and 43 mm. long.

Form: Generally urn-shaped with pointed tip.

Opening Rate: 1 to 2 days.

Color:

*When sepals first divide.*—Red RHS 43A.

*When petals begin to unfurl.*—Red RHS 43A.

Sepals: Hooded over the bud, but upstanding upon dividing.

*Shape.*—Generally oval, lobed and with an acute tip.

*Color.*—Inside — Whitish Green; outside — Blueish-Green, with Brownish tips when divided.

Calyx: Size — large.

*Shape.*—Funnel-shaped.

*Aspect.*—Smooth.

*Splitting.*—Rarely, about 1 or 2 percent of the flowers have a split calyx.

Peduncle: Erect, Blueish-Green in color.

THE FLOWER

Blooming habit: Continuous and profuse from Spring through Fall.

Size of bloom: Medium. Average diameter — 75 mm. Average depth — 58 mm.

Borne: Singly.

Shape: Flat topped, the form changing to be slightly high-centered as the bloom matures.

Petalage: Arrangement — alternate whorl.

*Form.*—Fan shaped, with undulate and slightly serrated margins.

*Texture.*—Soft.

*Appearance.*—Satiny.

*Color.*—Outer petals — Red RHS 43A with Light

Red a pinkish base. Inside petals — Red RHS 43A with Pinkish-White base.

Petaloids: None.

Peduncle: Sturdy and upright.

*Color.*—Blueish-Green.

Persistence: Petals hang on and dry.

Fragrance: None.

Lasting Quality:

*On plant.*—4 to 5 days.

*As cut flower.*—9 days.

REPRODUCTIVE ORGANS

Stamens: Anthers — 10 to 12 in number.

*Arrangement.*—Around the pistil.

*Filaments.*—18 mm. long. Color: White.

*Pollen.*—Color — Greyish-White.

Pistils: Number — 2.

*Styles.*—20 mm. long.

*Stigmas.*—Color — Pink to White.

Ovaries: 4 lobed.

This carnation plant is similar in its growth characteristics to its parent Crowley Sim and is to be noted for its long stems and high production of dark red flowers. The flower is flat in form and of medium size in comparison with CSU Red (unpatented) and Scania (unpatented), but develops virtually no splits or bullheads.

I claim:

1. A new and distinct variety of carnation plant, substantially as herein shown and described, characterized by its high production of medium sized red flowers borne on long sturdy stems, and by the very sparse occurrence of splits and bullheading.

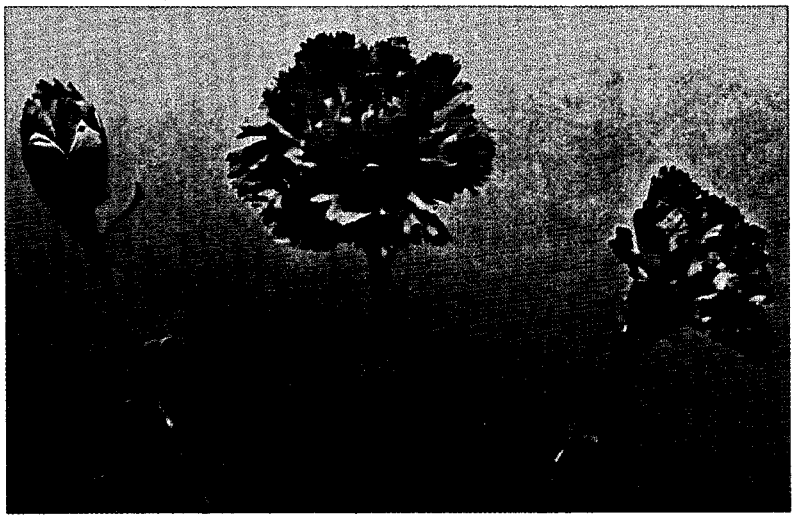

* * * * *